United States Patent
Sacherer

(10) Patent No.: US 7,833,477 B2
(45) Date of Patent: Nov. 16, 2010

(54) TAPE UNIT

(75) Inventor: Klaus-Dieter Sacherer, Kirchheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 329 days.

(21) Appl. No.: 12/020,667

(22) Filed: Jan. 28, 2008

(65) Prior Publication Data

US 2008/0185470 A1  Aug. 7, 2008

(30) Foreign Application Priority Data

Feb. 3, 2007  (EP) ................... 07002376

(51) Int. Cl.
*G01N 21/00* (2006.01)
*G01N 31/00* (2006.01)
*G01N 15/06* (2006.01)

(52) U.S. Cl. .................. 422/66; 422/61; 422/68.1; 436/43; 436/44; 436/63

(58) Field of Classification Search .................. 422/66; 436/44
See application file for complete search history.

(56) References Cited

U.S. PATENT DOCUMENTS

| | | | | |
|---|---|---|---|---|
| 4,954,319 A | * | 9/1990 | Koizumi et al. | 422/67 |
| 6,309,600 B1 | * | 10/2001 | Hunter | 422/66 |
| 7,378,270 B2 | * | 5/2008 | Azarnia et al. | 435/287.2 |
| 2006/0173380 A1 | * | 8/2006 | Hoenes et al. | 600/583 |
| 2006/0223078 A1 | * | 10/2006 | Changming et al. | 435/6 |

FOREIGN PATENT DOCUMENTS

| | | |
|---|---|---|
| EP | 0299517 B1 | 10/1993 |
| EP | 1267168 A1 | 12/2002 |
| EP | 1360935 B1 | 12/2006 |
| WO | 2004/047642 A1 | 6/2004 |

* cited by examiner

*Primary Examiner*—Brian J Sines
(74) *Attorney, Agent, or Firm*—Justin L. Sage; Roche Diagnostics Operations, Inc.

(57) ABSTRACT

A tape unit is provided comprising a flexible tape, a spool for unwinding unused tape and a spool for winding on used tape, wherein an intermediate section of tape which is located between the spools can be used by a user. The tape unit generally achieves a compact design by providing one of the spools in a receiving area defined within the other spool, and a deflection guide for guiding the tape from one spool to the other.

18 Claims, 4 Drawing Sheets

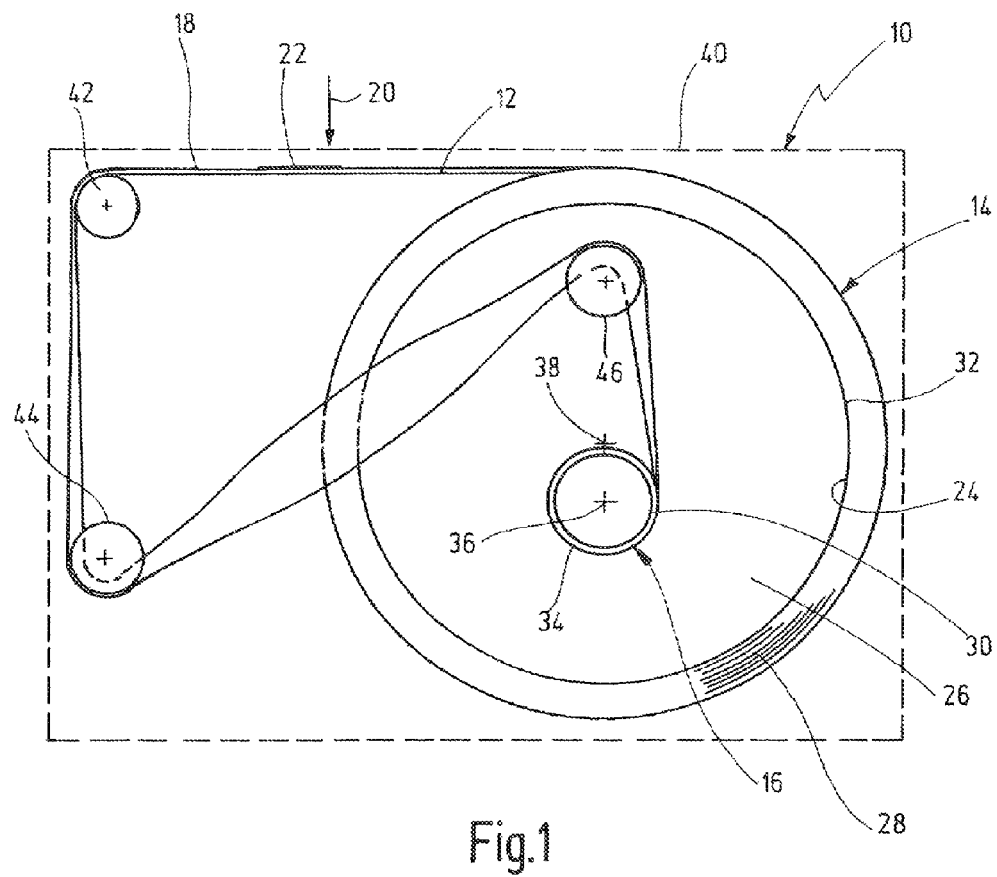
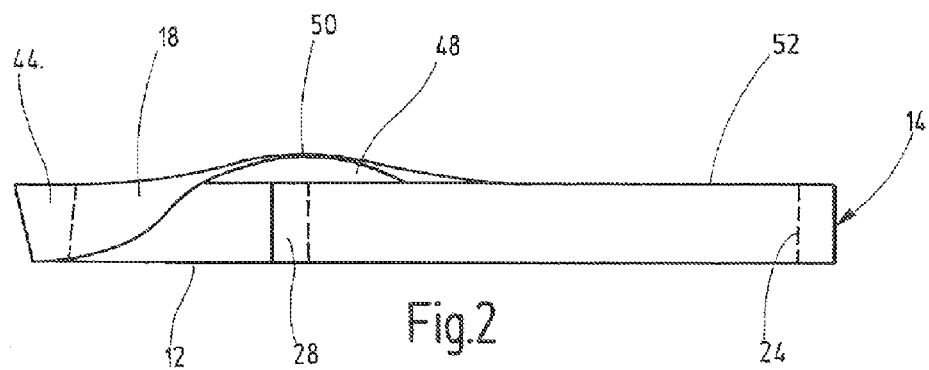

TAPE UNIT

PRIORITY CLAIM

The present application is based on and claims the priority benefit of European Patent Application No. 07002376.7, filed Feb. 3, 2007, which is hereby incorporated by reference in its entirety.

TECHNICAL FIELD OF THE INVENTION

The invention concerns a tape unit and in particular a tape cassette with a tape comprising diagnostic test elements and/or lancing elements which can be unwound from a first spool and wound onto a second spool wherein an intermediate section of tape located between the spools can be brought into use for a user.

BACKGROUND OF THE INVENTION

A test device with a tape unit for carrying out blood glucose tests is known in an earlier application WO2004/047642, which is hereby incorporated by reference herein in its entirety. It describes among other things a coaxial arrangement of spools lying laterally next to one another in order to utilize the limited total space available in a hand-held instrument as efficiently as possible. However, in this case the total height of the instrument is determined at least by the double tape width and additional thicknesses of intermediate walls.

On this basis, among the objects of the present invention is to further develop the tape cassette systems known in the prior art and to optimize a tape unit comprising diagnostic test elements and/or lancing elements that are unwound from a first spool and wound onto a second spool, with regard to a compact assembly, as well as to provide such a tape unit for an easy to handle instrument system.

SUMMARY OF THE PRESENT INVENTION

The above stated objects as well as other objects that will be apparent to those of ordinary skill in the art can be achieved generally by embodiments of the present invention. In particular, a tape unit is proposed to achieve this object, the tape unit comprising a tape, typically comprising a plurality of diagnostic test elements and/or lancing elements aligned in series, which can be unwound from a first spool and wound onto a second spool such that an intermediate section of the tape located between the spools can be used by a user, wherein one of the spools defines an interior receiving area and the other spool is provided within the receiving area. Advantageous embodiments and further developments of the invention will also be apparent from the disclosure herein.

The embodiments of the present invention are based on the idea of arranging the spools in a generally flat, co-planar and nested manner. Accordingly, it is proposed according to the present invention that one of the spools encloses an interior receiving area and that the other spool is provided within the receiving area. In this manner it is possible to achieve a further miniaturization and in particular a space-saving flat design. This also enables a reduction of the distances between the elements transported on the tape and thus ultimately also of the overall length of the tape.

In order to have the smallest possible overall height it has been discovered that one can provide the two spools to lie within each other in a generally co-planar level, wherein the receiving area is axially defined by the planar sides of the outermost spool.

In order to simplify the handling of the test unit of the present invention for a user, in one embodiment the two spools are stored in a housing and the tape unit formed in this manner is comprises a consumable tape cassette configured for use in a diagnostic device. Another improvement can be achieved when at least one of the spools has a core configured for receiving a tape coil and that can be rotated by a motor or by manual means.

In order to simplify the required tape deflections for guiding the tape from one spool to the other, in alternative embodiments the inner spool is arranged in the receiving area either eccentrically or concentrically relative to the surrounding outer spool so that the spool axes are spaced apart parallel to one another or lie on top of one another.

For embodiments of a test unit configured for use in a diagnostic device, a measuring chamber is defined by the spool located within the receiving area and is configured for a measuring unit designed to register with the tape. The measuring chamber typically is kept clear in the receiving area.

Another embodiment of the invention provides that the intermediate section of tape located between the spools is guided over one of the planar sides of the outermost spool by means of a deflection guide in order to enable tape transport between the outer and inner spool. In another embodiment, the deflection guide comprises first and second deflection elements for guiding the intermediate section of tape, the first deflection element being located outside of the receiving area and the second guide element being located within the receiving area.

In order to enable a longitudinal twist of the tape, in one embodiment the deflection elements are formed by deflection rollers having a somewhat conical shape, such as a truncated conical shape. A change in direction of tape transport can be thus be achieved by guiding the tape at at least one deflection point having two deflection edges having generally rounded surfaces which run generally non-parallel to one another.

Another improvement provides that the deflection guide has a transition structure for the tape located along a planar side of the spools and formed in one embodiment by a slide plane or a seal.

Furthermore, in order to achieve as flat a total structure as possible, in one embodiment the intermediate section of tape is guided over the planar side of the outer spool while twisting it longitudinally such that in a transition area the tape section runs generally parallel to the planar side of the spool.

In various embodiments, the tape comprises a series of diagnostic test elements. In one such embodiment, each test element comprises a diagnostic or analytical field on which a test fluid such as a body fluid, e.g. blood, can be applied, when each successive test field arrives at an application site when the tape is advanced (unwound from one spool and wound on the other spool). Generally speaking, it is the intermediate section of the tape which arrives at the application site for applying the test fluid.

In other embodiments, the tape comprises a series of lancing elements transported by means of the tape and provided at an application site on the intermediate section of tape. In one embodiment, both types of tapes can be provided in order to provide a magazine system to be employed for a plurality of medical diagnostic/analysis tests, e.g. blood glucose tests.

For the longest possible shelf-life, in one embodiment the first spool carrying unused tape is sealed off from the receiving area, from the environment, and especially from the entry of moisture.

The present invention also generally concerns a diagnostic system with a tape unit as described above wherein at least one spool of the tape unit can be rotated by a motor or manually in order to successively bring the particular elements stored on the tape into use.

BRIEF DESCRIPTION OF THE DRAWINGS

Further advantages and embodiments of the invention arise from the description and the enclosed drawings. The invention is described in more detail below on the basis of illustrative embodiments. However, the invention is not limited to the illustrative embodiments given here. The illustrative embodiments are shown schematically in the figures. Identical reference numbers in the individual figures designate elements which are identical or whose functions are identical, or which correspond to one another in terms of their function.

FIG. 1 shows a top plan view of an embodiment of a tape unit with spools arranged within one another according to the present invention.

FIG. 2 shows a side plan view of the embodiment of a tape unit shown in FIG. 1.

DETAILED DESCRIPTION OF EMBODIMENTS OF THE PRESENT INVENTION

Figure 3:
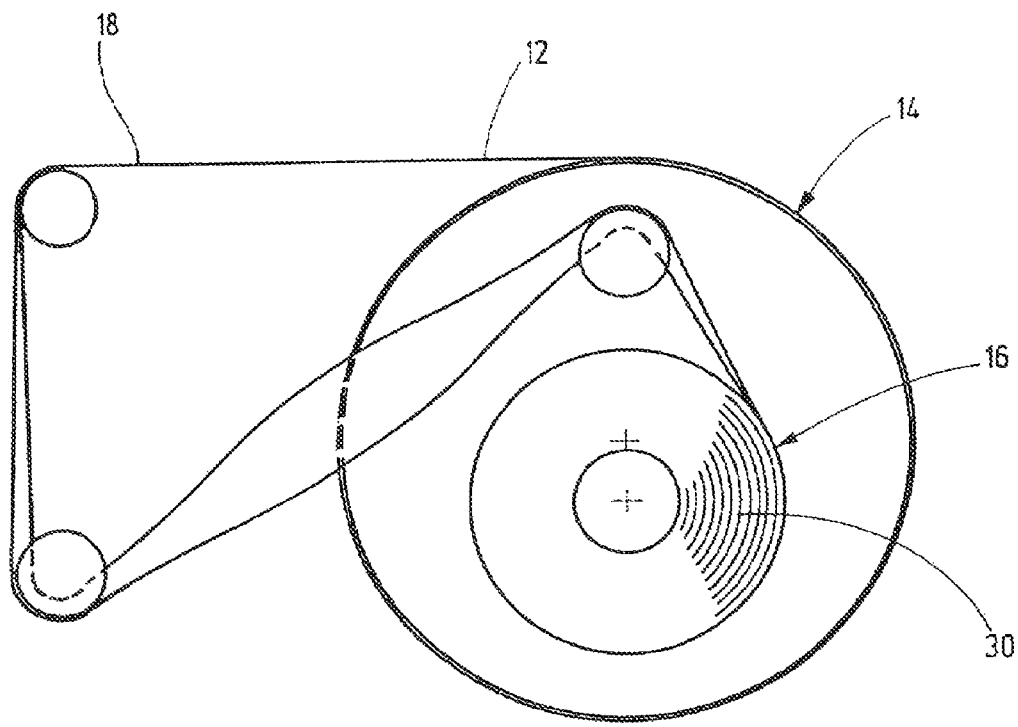
FIG. 3 shows a top plan view of a pre-spooled tape unit according to one embodiment of the present invention.

It is understood that the aforementioned and the following exemplified characteristics are applicable not only in the specified combination, but also in other combinations or in isolation, without departing from the scope of the present invention.

Referring to FIG. 1, the diagnostic tape unit 10 comprises a flexible tape 12, an unwind spool 14 for unwinding unused tape, and a take-up spool 16 for winding-on used test tape. Unwind spool 14 carries outer tape coil 28, and take-up spool 16 carries inner tape coil 30, each of which tape coils 28, 30 are formed from the tape 12 being coiled around the particular spool. Intermediate section of tape 18 is located between the spools 14, 16 and can be brought into use at an application site (arrow 20). The location and function of the application site is as desired based on the nature or type of flexible tape 12 provided in the unit 10. In one embodiment, the tape 12 comprises a series of analytical test fields 22 located in sections on the tape 12 and can be loaded with a test fluid, e.g. blood, in order to detect an analyte, e.g. glucose. In other embodiments, such a tape unit 10 is configured for use within a test system such as in a hand-held device (not shown) in which the test fields 22 can be successively made available by winding the tape manually or by a rotary drive that can be coupled to the take-up spool 16.

Referring now to FIGS. 1 and 3, in one embodiment an inner ring surface 24 of the unwind spool 14 encloses a central receiving area 26 in which the take-up spool 16 is arranged in order to achieve the desired compact design for the tape unit 10. The spools 14, 16 and the tape coils 28, 30 formed from the tape 12 thus lie generally co-planar within each other, i.e. on the generally same plane or level. As in the embodiment shown, the inner diameter 32 of the unwind spool 14 is sufficiently larger than the outer diameter 34 of the take-up spool 16 so that a sufficiently large receiving area 26 is available for tape coil 30 as it increases in size when the tape 12 advances, as shown in FIG. 3. In one embodiment, the take-up spool 16 is arranged generally eccentrically within the unwind spool 14 and the relevant spool axes 36, 38 (FIG. 1) are spaced apart and run generally parallel to one another.

In the embodiment shown in FIG. 1, the intermediate section of tape 18 is guided within the housing 40 over three deflection rollers 42, 44, 46. As shown in FIG. 2, the two deflection rollers 44, 46 together with the transition piece 48 as a deflection guide ensure that the intermediate section of tape 18 is guided in a flat manner over the outer tape coil 28. For this purpose, in the shown embodiment the deflection rollers 44, 46 are generally conically shaped so that in the apex of the slide surface 50 of the transition piece 48, the tape 12 is rotated or longitudinally twisted by 90°. Thus in the upper twisting area the tape runs generally perpendicular to the spool axes 36, 38 and generally parallel to the planar face 52 of the spool 14 on the transition side. It is also conceivable that an opening in the housing 40 is present in this area as an application site 20.

In other embodiments, instead of test fields 22, the tape 12 comprises a series of lancing elements (not shown) configured for lancing an area of skin of a user in order to obtain a biological test fluid, e.g. blood, for dispensing at the application site 20. In yet other embodiments, lancing elements and test fields 22 are arranged in a combined manner on the tape 12 in order to further simplify the processes for a blood glucose test (lancing followed by sampling and measuring).

Figure 4:
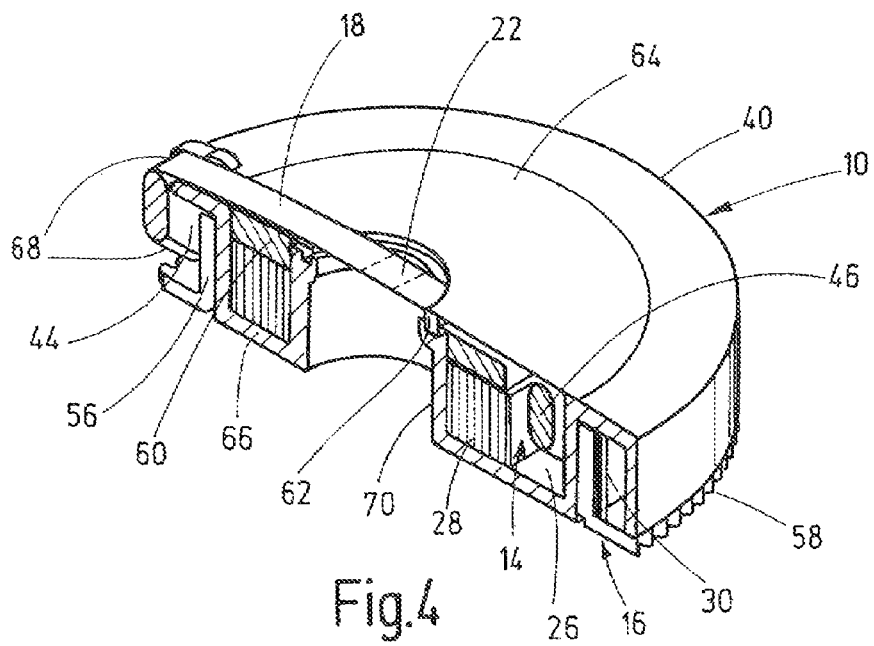
FIG. 4 shows a perspective and cross-sectional view of a further embodiment of a compact tape unit illustrating an axial section.
Figure 5:
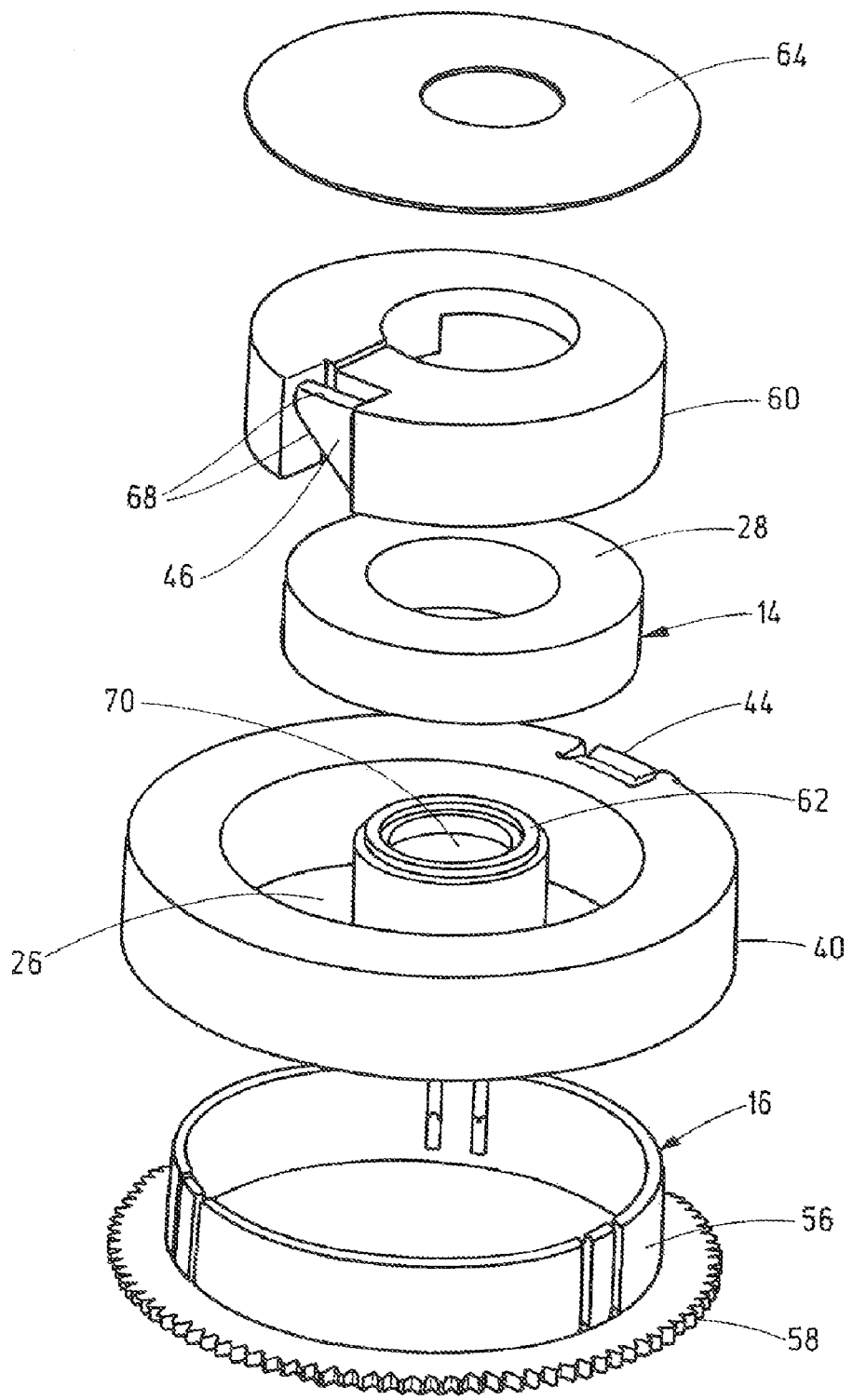
FIG. 5 shows an exploded diagram view of the components of the tape unit according to FIG. 4.

FIGS. 4 and 5 illustrate a different embodiment according to the present invention. (In FIGS. 4-5, corresponding components are labeled with the same reference numerals as described above with regard to other embodiments.) FIG. 4 shows a particularly compact design similar to a doughnut. The individual components can be seen best in the exploded view of FIG. 5. The spools 14, 16 in this embodiment are arranged generally concentrically relative to one another in a ring-shaped housing 40. In this case the unwind spool 14 is the inner spool and generally comprises tape coil 28 forming the unused portion of the tape 12, while the take-up spool 16 is the outer spool and is provided for winding up used tape. For this purpose the take-up spool 16 has a core 56 which can be rotated by a toothed ring 58 provided in the illustrated embodiment on the outer edge of the back face of spool 16. In this case the tape 12 is transitioned radially as an intermediate section of tape 18.

In this embodiment, the deflection guide comprises a first deflection piece 44 formed on the housing 40 and a second deflection piece 46 moulded onto a housing insert 60 formed from a desiccant as well as a sealing ring 62. A cap 64 ensures the cover of the receiving area 26 is sealed tight against the housing bottom 66 from the entry of moisture. Also in this case planes that are defined by the planar sides of the up-take tape coil 30 define the axial boundary of the receiving area 26 so that the tape coils 28, 30 again lie within each other at the same level. In order to enable a tape deflection at the front face, the deflection pieces 44, 46 each have two generally rounded deflection edges 68 which run towards each other at an acute angle over which the tape 12 can in each case be deflected by 90° from its current transport direction. In this manner the tape 12 can be spooled off or wound on tangentially to the tape coils 28, 30 as it passes over the take-up spool 16 in its radial direction.

In one embodiment, in order to optically scan or otherwise register test fields 22 present on a tape 12, a measuring chamber 70 is kept generally open in the interior of the housing 40 in which an appropriate measuring unit of the instrument (not shown) engages when unit 10 is inserted into a corresponding diagnostic or analysis device or system for which it is configured for use.

Figure 6:
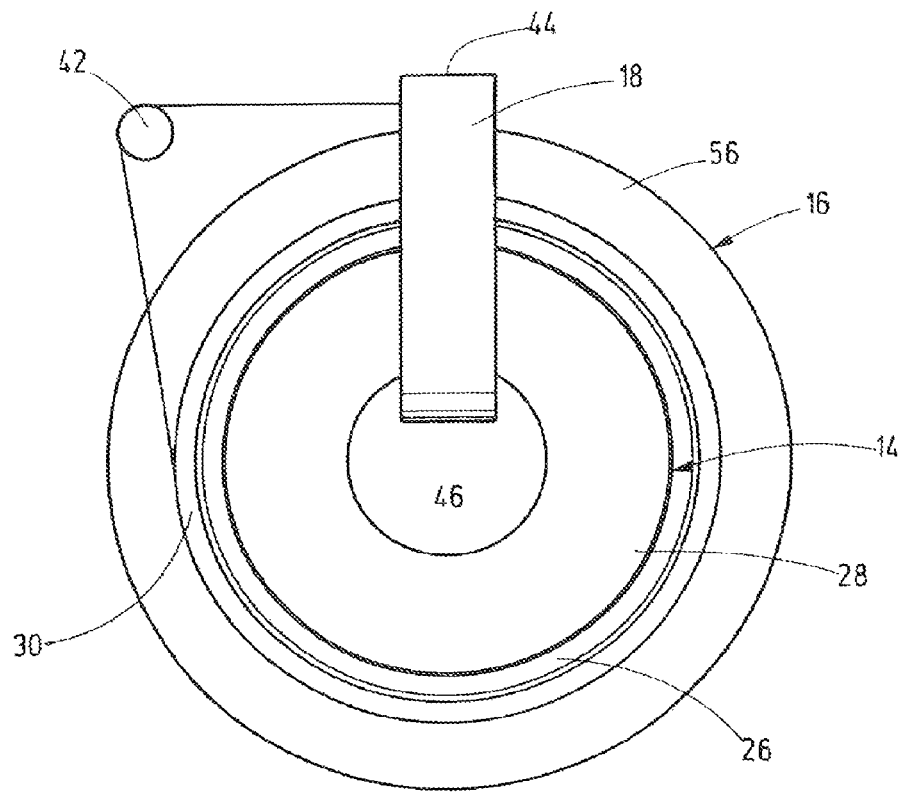
FIG. 6 shows a top plan view of another embodiment of a tape unit according to the present invention having spools arranged within one another.
Figure 7:
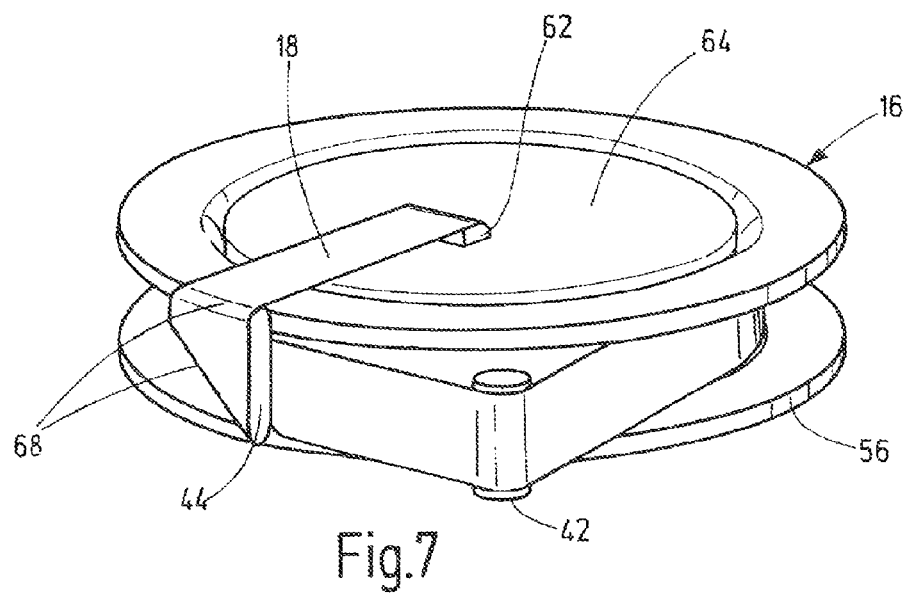
FIG. 7 show a perspective view of the embodiment of a tape unit shown in FIG. 6.

FIGS. 6 and 7 show yet another embodiment of a tape-in-tape arrangement according to the present invention whereby in this case (as in the embodiment of FIGS. 4-5) the unused tape 12 is spooled from the interior of the tape coil 28 of the unwind spool 14. Two deflection pieces 44, 46 with deflection edges 68 that angle towards one another are also provided for the tape deflection. The receiving area 26 is closed on the planar side by a cap 64 that is only shown in FIG. 7, through which the tape 12 is guided over a seal 62.

The features disclosed in the above description, the claims and the drawings may be important both individually and in any combination with one another for implementing the present invention in its various embodiments.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. A tape unit comprising a tape coiled around an unwind spool and a take-up spool and having an intermediate section of tape located between the spools and positioned by the tape unit for use by a user, wherein one of the unwind spool and the take-up spool comprises an outermost spool having an inner wall enclosing an interior receiving area, and wherein the other of the unwind spool and the take-up spool is provided within the receiving area.

2. The tape unit according to claim 1, wherein the unwind spool and the take-up spool are generally co-planar and wherein the receiving area is axially defined by planar sides of the outermost spool.

3. The tape unit according to claim 1, wherein the spools are located in a housing, the tape unit comprising a consumable tape cassette configured for use in a diagnostic device.

4. The tape unit according to claim 1, wherein at least one of the spools comprises a core configured for carrying a tape coil and for being rotated by a motor or manual arrangement.

5. The tape unit according to claim 1, wherein the spool located in the receiving area is arranged one of eccentrically and concentrically relative to the outermost spool.

6. The tape unit according to claim 1, wherein the tape comprises a series of test fields for analysis of a test fluid, the tape unit further comprising a measuring chamber defined within the spool located in the receiving area, the measuring chamber configured for receiving a measuring unit configured to register with one of the test fields for performing analysis thereon.

7. The tape unit according to claim 1, further comprising a deflection guide configured for guiding the intermediate section over a planar side of the outermost spool.

8. The tape unit according to claim 7, wherein the deflection guide comprises a first deflection element located outside of the receiving area and a second guide element located within the receiving area, the intermediate section being guided over each of the first and second deflection elements.

9. The tape unit according to claim 8, wherein the first and second deflection elements each comprise a deflection roller having a generally conical shape.

10. The tape unit according to claim 9, wherein the first and second deflection elements each comprise a deflection roller having a generally truncated conical shape.

11. The tape unit according to claim 7, wherein the deflection guide comprises at least one deflection point, each deflection point comprising first and second deflection edges having generally rounded surfaces, the surfaces of the first and second deflection edges being configured to be generally non-parallel to each other.

12. The tape unit according to claim 7, wherein the deflection guide comprises a transition structure located along a planar face of the outermost spool configured for transitioning the tape between the take-up spool and the unwind spool, the transition structure comprising one of a slide surface and a seal.

13. The tape unit according to claim 1, wherein the intermediate section is passed over a planar side of the outermost spool, the unit being configured for twisting the intermediate section longitudinally in a transition area such that the intermediate section runs generally parallel to the planar side of the spool.

14. The tape unit according to claim 1, wherein the tape comprises a plurality of sections each having an analytical test field, and wherein the tape unit is configured and arranged with an application site at which a test fluid can be applied to successive test fields in the intermediate section as the tape is advanced from the unwind spool to the take-up spool.

15. The tape unit according to claim 1, wherein the tape comprises a plurality of lancing elements, and wherein the tape unit is configured and arranged with an application site at which one of the lancing elements in the intermediate section can be provided for use.

16. The tape unit according to claim 1, wherein the unwind spool is configured to carry a tape coil comprising an unused portion of the tape, and wherein the tape unit is configured for sealing the unused portion from the environment.

17. The tape unit according to claim 16, wherein the unwind spool is the spool located within the receiving area, the receiving area configured for sealing the unused portion from the environment.

18. A diagnostic system for performing a diagnostic analysis on a test fluid, the system comprising tape unit comprising a tape coiled around an unwind spool and a take-up spool and having an intermediate section of tape located between the spools and positioned by the tape unit for use by a user of the system, wherein one of the unwind spool and the take-up spool comprises an outermost spool having an inner wall enclosing an interior receiving area, and wherein the other of the unwind spool and the take-up spool is provided within the receiving area, the tape comprising a plurality of sections each having an analytical test field, and wherein the tape unit is configured and arranged with an application site at which the test fluid can be applied to successive test fields in the intermediate section as the tape is advanced from the unwind spool to the take-up spool, and wherein at least one of the spools is configured for being rotated by a motor or by manual means.

* * * * *